United States Patent [19]

Murray et al.

[11] Patent Number: 5,336,684
[45] Date of Patent: Aug. 9, 1994

[54] OXIDATION PRODUCTS OF CEPHALOMANNINE

[75] Inventors: Christopher K. Murray; Jeffrey T. Beckvermit; Timothy D. Ziebarth, all of Boulder, Colo.

[73] Assignee: Hauser Chemical Research, Inc., Boulder, Colo.

[21] Appl. No.: 53,902

[22] Filed: Apr. 26, 1993

[51] Int. Cl.$^5$ .................. A61K 31/335; C07D 305/14
[52] U.S. Cl. .................................. 514/449; 544/172; 549/510; 549/511
[58] Field of Search ................. 549/510, 511; 544/172; 514/449

[56] References Cited

U.S. PATENT DOCUMENTS

| | | | |
|---|---|---|---|
| 4,814,470 | 3/1989 | Colin | 549/510 |
| 4,857,653 | 8/1989 | Colin | 549/510 |
| 4,876,399 | 10/1989 | Holton | 549/510 |
| 4,924,011 | 5/1990 | Denis | 549/510 |
| 4,942,184 | 7/1990 | Haugwitz | 549/510 |
| 4,960,790 | 10/1990 | Stella | 549/510 |
| 5,019,504 | 5/1991 | Christen | 435/123 |
| 5,059,699 | 10/1991 | Kingston | 549/511 |

OTHER PUBLICATIONS

PCT WO 92/13961, Saito et al, "Process for Producing Taxol by Cell Culture of Taxus Species", Aug. 1992.
PCT WO 92/07842, RAO "Method for the Isolation and Purification of Taxane Derivatives", May 1992.
Streitwieser et al., "Introduction to Organic Chemistry", 3rd edition, pp. 266 and 366 1985.
Kingston et al., "Modified Taxols. A Method for the Separation of Taxol and Cephalomannine," J. Nat. Product, 1991.
J. Org. Chem., 1981, vol. 46, No. 19 3936-3938, 1981.
"Nature," vol. 277, Feb. 1979, pp. 665-667.
"Ozonolysis-A Modern Method in the Chemistry of Olefins," Russian Chemical Reviews, 50 (7), 1981, pp. 636-651.
"Synthesis of Biologically Active Taxol Analogues with Modified Phenylisoserine," J. Med. Chem., 1992, 35, 4230-4237.

*Primary Examiner*—C. Warren Ivy
*Assistant Examiner*—Ba K. Trinh
*Attorney, Agent, or Firm*—Dean P. Edmundson

[57] ABSTRACT

Antineoplastic taxol derivatives are derived by selective oxidation of the alkene portion of the side chain of cephalomannine. The derivative displays high activity in promoting assembly of microtubulin and also displays cytotoxic activity against malignant cells.

5 Claims, 6 Drawing Sheets

1  R = C$_6$H$_5$CO, R' = Ac   taxol
2  R = C$_4$H$_9$OCO, R' = H   taxotere
3  R = CH$_3$CH=CCO, R' = Ac   cephalomannine
        |
        CH$_3$ 1  R = C₆H₅CO, R' = Ac   taxol 2  R = C₄H₉OCO, R' = H   taxotere 3  R = CH₃CH=CCO, R' = Ac   cephalomannine
           |
           CH₃

OXIDATION PRODUCTS OF CEPHALOMANNINE

FIELD OF THE INVENTION

This invention relates to taxane derivatives. More particularly, this invention relates to oxidation products of cephalomannine. In another aspect, this invention relates to techniques for producing taxol derivatives from cephalomannine.

BACKGROUND OF THE INVENTION

Taxol, 1, a material occurring in nature, and extracted from *Taxus brevifolia* (i.e., the Pacific yew tree) and other biomass has been identified as having significant tubulin binding (Schiff, P. B. et al., "Promotion of Microtubule Assembly in vitro by Taxol," *Nature*, Vol. 277:665–67 (February 1979)) and, when delivered to the cell, cytotoxic activity which has been demonstrated through Phase III clinical trials. Taxol was recently approved for the treatment of refractory ovarian cancer by the Food and Drug Administration.

Taxotere, 2, a semisynthetic derivative of taxol with improved water solubility, has been compared with taxol in Phase I clinical trials. Taxotere is slightly more active as a promoter of tubulin polymerization, 1.5-fold more potent as an inhibitor of replication in mouse macrophage-like J774.2 cells and in P388 murine leukemia cells, and at least fivefold more potent in taxol resistant tumor cells (Pazdur, R. et al., "Phase I Trial of Taxotere: Five-Day Schedule", *Journal of the National Cancer Institute*, 1781, (1992)). The structural differences between taxol 1 and taxotere 2 are minor (see FIG. 1), yet enhanced in vitro tubulin binding activity is observed for taxotere.

Consequently, it is difficult to predict the relative potency of a taxol analogue for microtubulin polymerization activity based on small changes in the overall structure. An examination of Kingston's Review, (Kingston, D. G. I., "The Chemistry of Taxol", *Pharmacology and Therapeutics*, 52:1–34, (1991)), provides an overall view of the complexity of the structure-activity relationship of taxol analogues. It is clear that minor structural changes can cause major changes in tubulin binding activity and cytotoxicity. These changes can even completely eliminate activity. In addition, other factors such as greater water solubility and lower toxicity exist, which must be strongly considered when evaluating the efficacious nature of therapeutic agents.

The novel synthetic taxol derivatives described herein have not heretofore been described nor has the literature suggested that such new derivatives would exhibit tubulin assembly or advantageous cytotoxic activity.

SUMMARY OF THE PRESENT INVENTION

There has now been discovered a new compound that displays in vitro tubulin binding and cytotoxic activity similar to taxol. The new antineoplastic taxol derivative is derived by selective oxidation of the alkene portion of the side chain of cephalomannine 3. The formation of this new taxol derivative from cephalomannine has not been described previously and provides in high yield the new derivative.

It is an object of this invention to provide a new semisynthetic taxol derivative that displays unexpectedly high activity in promoting the assembly of microtubulin in vitro and cytotoxic activity against B16 melanoma cells, for example.

It is another object of this invention to provide a pharmaceutical composition which is effective in inhibiting the growth of tumor cells.

It is a further object of this invention to provide methods for producing the new taxol derivative.

Other objects and advantages of the present invention will be apparent from the following detailed description and the accompanying drawings.

DESCRIPTION OF THE INVENTION AND THE PREFERRED EMBODIMENT

This invention relates to the treatment of cephalomannine 3, a close natural analogue of taxol, with a strong oxidizing agent, e.g. ozone, to generate in good yield a new derivative mixture. The cephalomannine starting material can be isolated in a conventional manner such as described in a recent publication (Rao, Koppaka V., "Method for the Isolation and Purification of Taxane Derivatives", International Publication Number, WO 92/07842, May 14, 1992), incorporated herein by reference.

Figure 1:
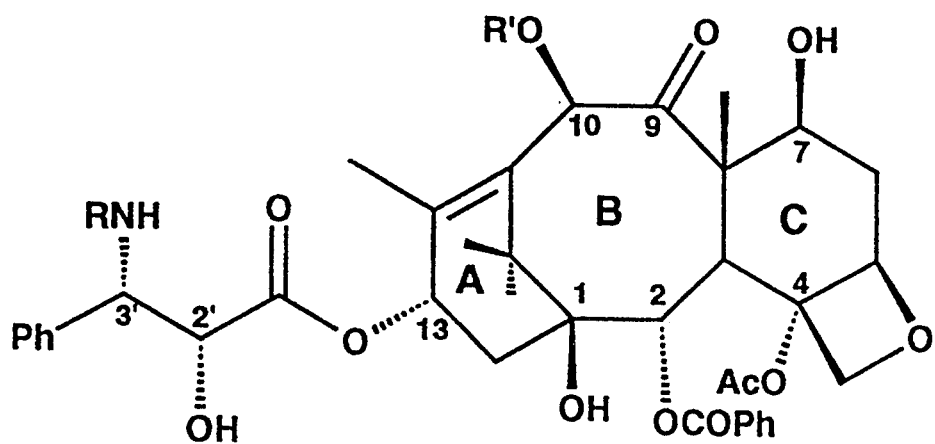
FIG. 1 is a diagram showing structural differences between taxol, taxotere and cephalomannine.
Figure 2:
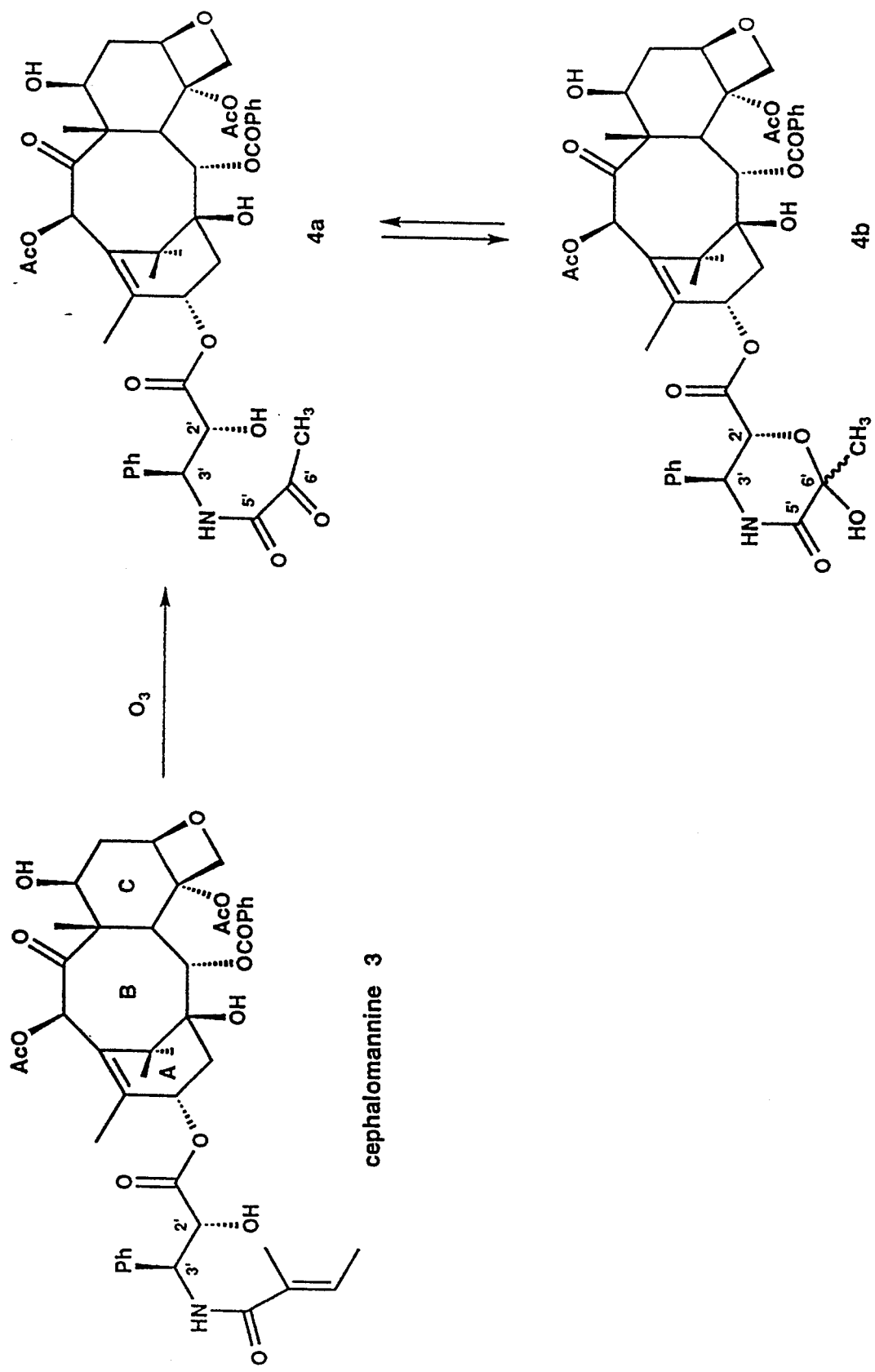
FIG. 2 is a reaction scheme for cephalomannine and ozone.

Treatment of an ether and/or hydrocarbon and/or alcoholic and/or chlorinated solvent solution of cephalomannine between −78° C. and room temperature, with 5 to 1000 equivalents of ozone, followed by purging with an inert gas, results in the formation of the α-ketoamide(pyruvamide)/α-ketal-amide derivative mixture 4a, 4b (see FIG. 2). The transformation is very selective for the side chain alkene and over-oxidation can be avoided, i.e., oxidation of the tetrasubstituted alkene in ring A and other functional groups can be prevented, if an amount of ozone is added which is sufficient to completely oxidize the tiglate amide functional group (see R for compound 3 of FIG. 1), while also avoiding oxidation elsewhere in the molecule. The correct stoichiometry is determined by calibrating the ozone generator and by monitoring the reaction using high pressure liquid chromatography (HPLC). A description of the method for monitoring reactions by HPLC is contained in the Examples section below.

The new synthetically modified taxane derivative mixture, hereafter designated 4ab, was characterized by spectroscopic analysis. The $^1$H-NMR and $^{13}$C-NMR spectra of the equilibrium mixture shows both 4a and 4b present in a ratio of 4:1 in chloroform-d ($CDCl_3$). When the compounds are analyzed by $^{13}$C-NMR in methyl-$d_3$ alcohol-d ($CD_3OD$), the ratio changes to approximately 1:1. In $CDCl_3$ solvent, the ketone (6'-4a) carbonyl resonance at 195.4 ppm is approximately four times larger than the hemiketal (6'-4b) carbon resonances at 102.5 and 105.4 ppm (two diastereomers for 4b). In $CD_3OD$ solvent, the ketone (6'-4a) carbonyl resonance at 197.2 ppm is approximately the same peak height (non-quantitative $^{13}$C-NMR experiment) as the ketal/hemiketal carbon resonances at 97.9, 101.9, 104.2, 105.1, and 106.5 ppm. The five different ketal/hemiketal carbon resonances in CD$_3$OD are attributed to the diastereomeric ketal carbons represented in 4b, and solvent addition to the open and closed forms of 4ab. It should be emphasized here that the two forms 4a and 4b are rapidly interconverting in solution at room temperature. Isolation of exclusively one form from the other without resorting to chemical conversion of the mixture has not been observed.

Figure 3:
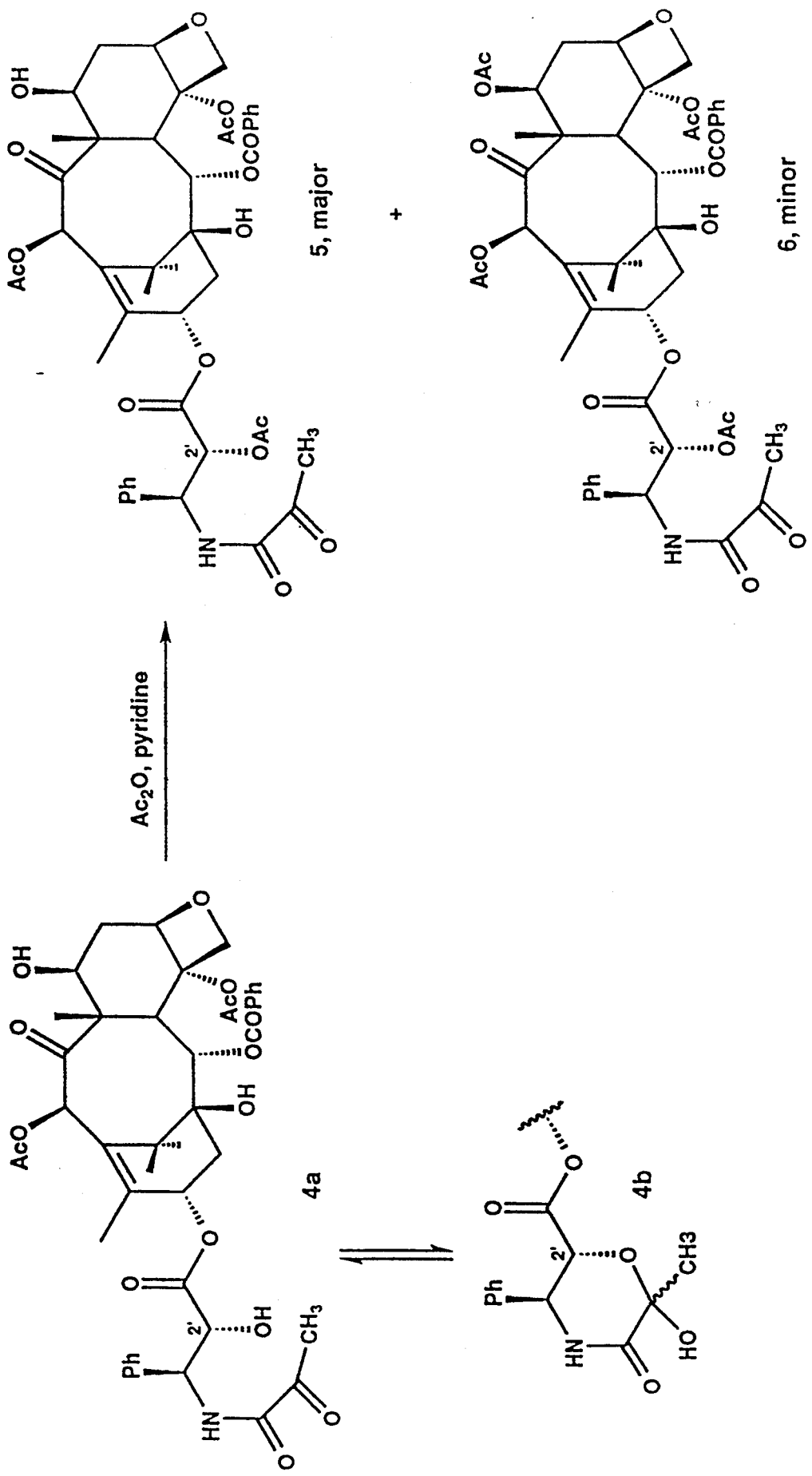
FIG. 3 is a reaction scheme for treatment of a reaction mixture with acetic anhydride.
Figure 4:
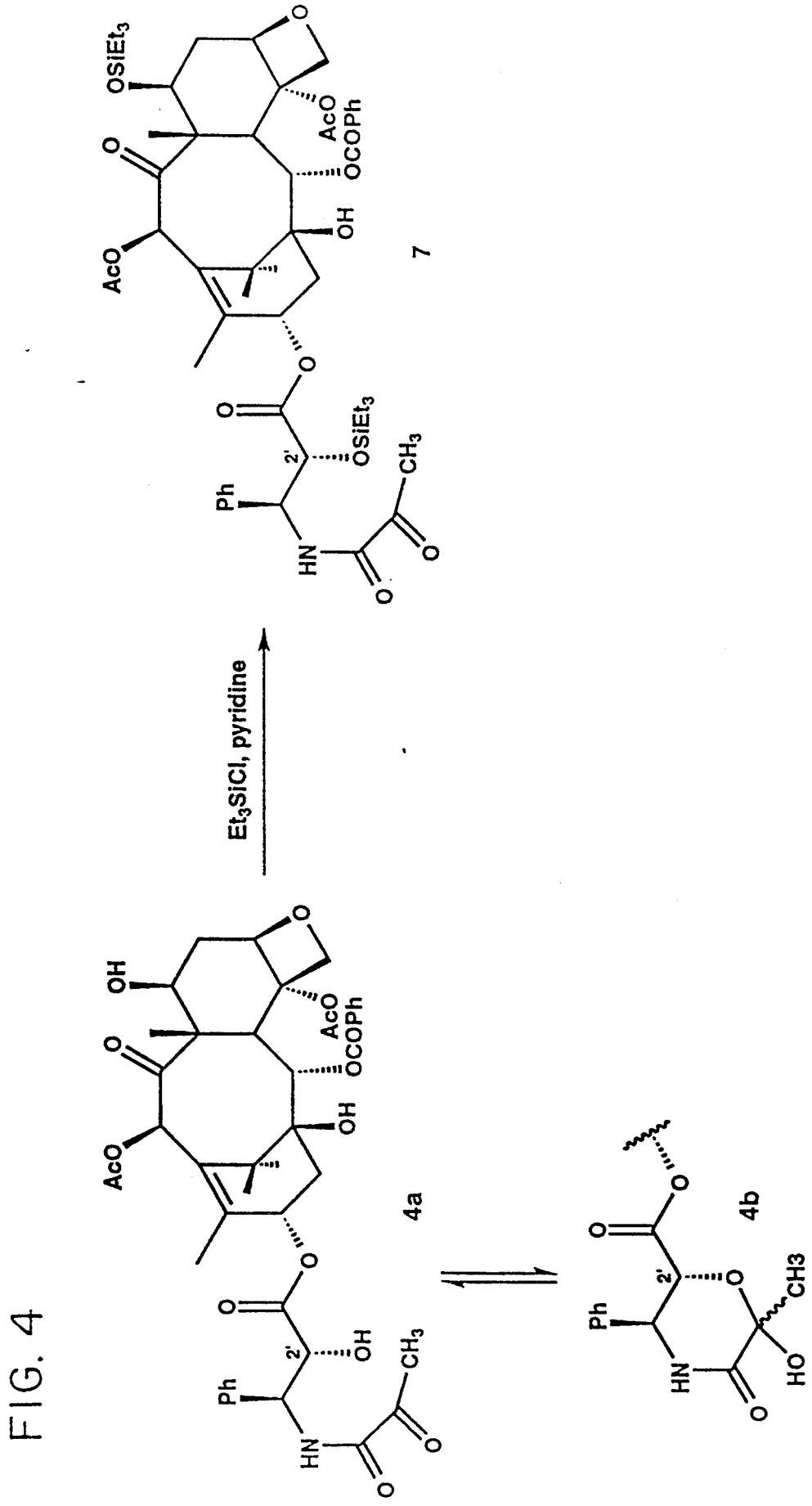
FIG. 4 is a reaction scheme for treatment of a reaction mixture with triethylsilyl chloride.

The new synthetic taxane derivative mixture 4ab was characterized by chemical conversion to other new taxane derivatives. The crude ozonolysis reaction mixture was treated with acetic anhydride in pyridine (see FIG. 3) to generate the two compounds shown (5 and 6). The 2'-OH is acetylated in both compounds as shown so the equilibrium between open and closed forms for the starting material (4ab) is not possible. A similar result was observed upon silylation using triethylsilyl chloride in pyridine (see FIG. 4). The triethylsilyl derivative 7 cannot cyclize because the 2'-OH is blocked. All of the compounds described here were characterized by spectroscopic techniques (for synthesis method and characterization data see the section below titled Examples).

Figure 5:
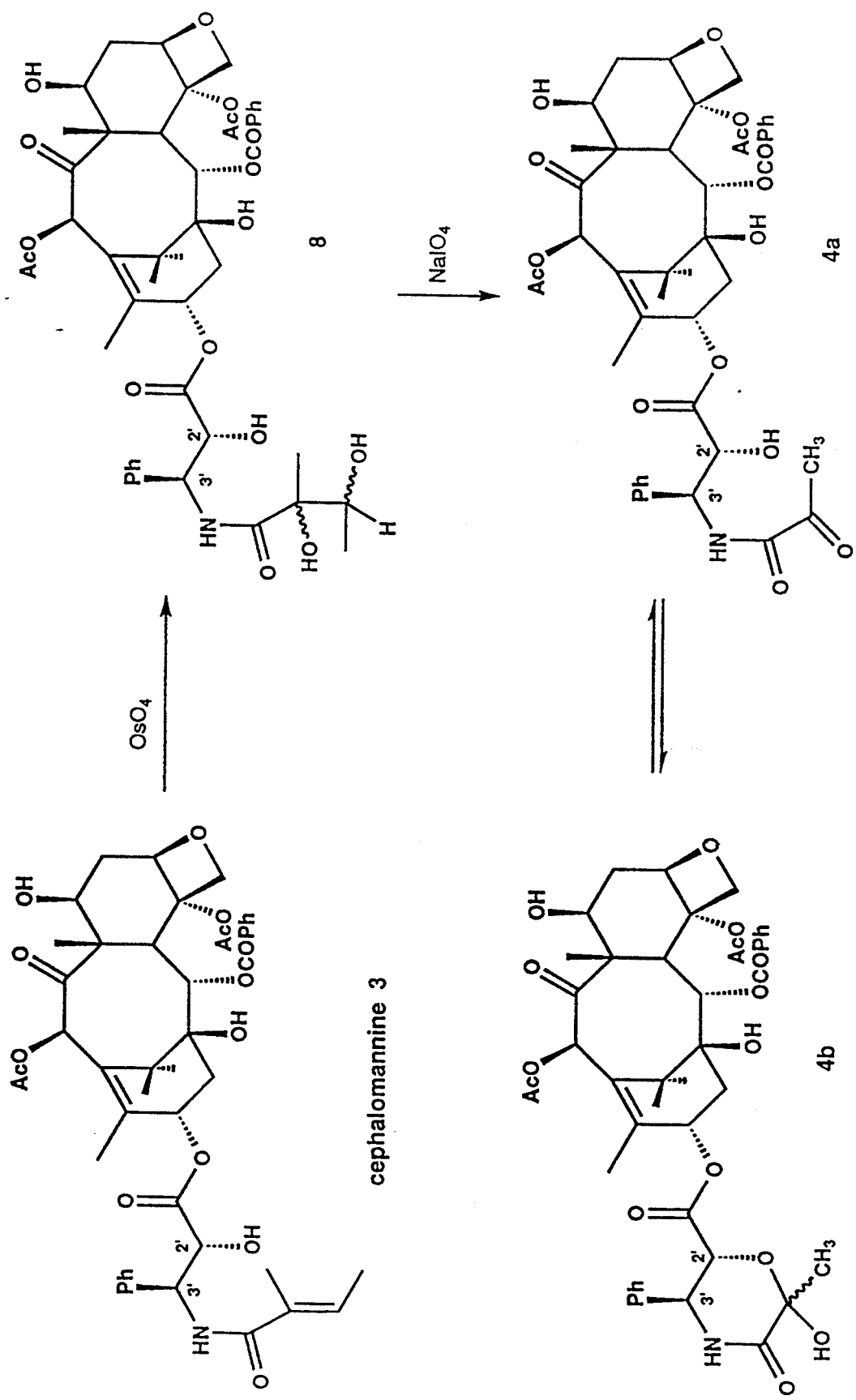
FIG. 5 is a reaction scheme for cephalomannine and osmium tetroxide.

The new synthetic taxane derivative mixture 4ab was synthesized by an additional method of organic chemical synthesis from a different starting material. As shown in FIG. 5, the diol 8 is available via dihydroxylation of cephalomannine using established methodology (Kingston, D. G. I., et al, "Modified Taxols, 7. A Method for the Separation of Taxol and Cephalomannine", *J. Nat. Prod.* 55: pp 259–261, (1992)), incorporated herein by reference. When the diol 8 is treated with sodium periodate, the expected compound 4a (in equilibrium with the cyclized form 4b), is formed in very good yield. The oxidative cleavage of a vicinal diol functional group similar to the side-chain portion of 8, is known to yield carbonyl compounds similar to the ketoamide group of 4a (Sklarz, B., "Organic Chemistry of Periodates", *Quarterly Reviews*, pp 3–28, (1967)), incorporated herein by reference. The methodology described here is another structure proof of 4ab. The synthesis method shown in FIG. 5 provides a product mixture with identical spectral and chromatographic analyses as the product mixture from reacting ozone with cephalomannine (see FIG. 2).

The cleavage of the diol functional group in compound 8 is achieved by using an effective amount of an oxidizing agent. Effective oxidizing agents include, but are not limited to, periodic acid and salts thereof, lead tetraacetate, sodium bismuthate, tetrabutylammonium periodate, manganese dioxide, pyridinium chlorochromate, and potassium permanganate. The oxidizing agents listed are not ranked according to effectiveness in performing the oxidation step. The relative effectiveness of the various possible oxidizing agents depends upon the concentration employed and other conditions of the reaction.

Figure 6:
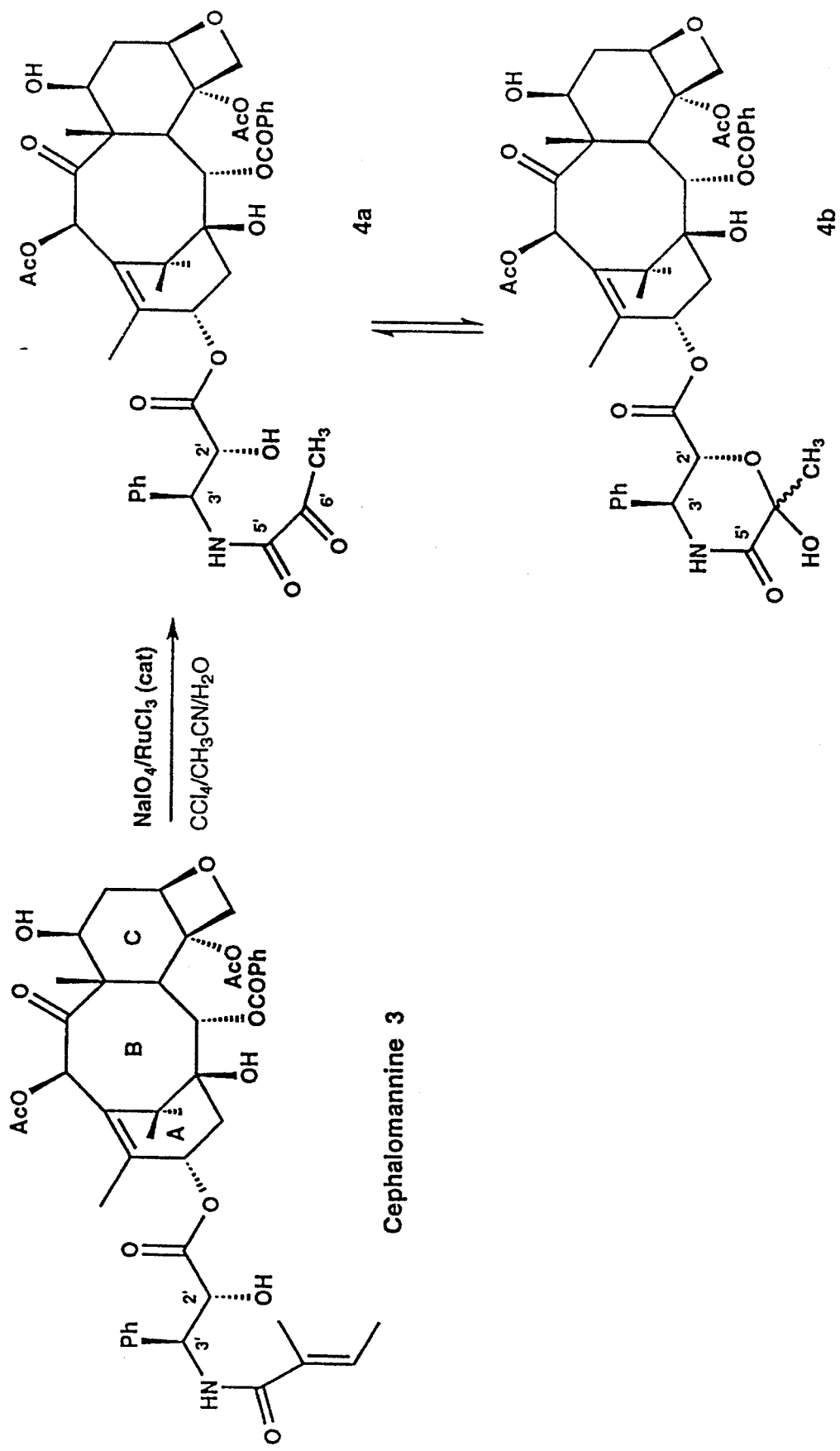
FIG. 6 is a reaction scheme for cephalomannine and $NaIO_4$.

The new synthetic taxane derivative mixture 4ab was also synthesized by a variation on the two-step method shown in FIG. 5. Treatment of compound 3 in a two-phase solvent system as shown in FIG. 6, with sodium periodate and ruthenium trichloride catalyst, results in a mixture with identical chromatographic and spectral (ultraviolet) characteristics to 4ab. The sodium periodate/ruthenium trichloride oxidative cleavage of an internal alkene functional group similar to the side-chain portion of 3, is known to yield carbonyl compounds similar to the ketoamide group of 4a (Carlsen, P. H. J., et al., "A Greatly Improved Procedure for Ruthenium Tetraoxide Catalyzed Oxidations of Organic Compounds", *J. Org. Chem.*, pp 3936–3938, (1981)), incorporated herein by reference. In a similar manner, other transition metal catalysts that are capable of diol oxidation when used in combination with oxidants such as periodate or hydroperoxide, can be used for the oxidative cleavage of the alkene portion of the side chain of cephalomannine. The ruthenium trichloride/periodate oxidation methodology described here constitutes another structure proof of 4ab, and provides a third oxidation method for the synthesis of 4ab from cephalomannine 3.

The new compound mixture, 4ab, shows good tubulin binding and cytotoxicity activity with in vitro testing. The in vitro test results are comparable to results for taxol. Tubulin binding and cytotoxicity data for cephalomannine and the synthetic derivatives described herein are included for comparison. The tubulin testing was done exactly as described by Himes (Georg, G. I., et al., "Synthesis of Biologically Active Taxol Analogues with Modified Phenylisoserine Side Chains", *J. Med. Chem.* Vol 35:4230, (1992)), incorporated herein by reference. See Table 1 for the data. Taxol has been included in Table 1 for reference. In addition, each sample is compared to taxol in the columns: ED$_{50}$/ED$_{50}$ Taxol (for Tubulin Assembly), and ED$_{50}$/ED$_{50}$ Taxol (for B16 Proliferation); taxol shows a value of approximately 1 in these columns. A number less than 1 in these columns indicates greater activity than taxol. A number greater than 1 in these columns indicates lower activity than taxol. The error in the tests appears to be $\pm$10–20%. The data clearly shows that the $\alpha$-ketoamide-taxane mixture 4ab has activity comparable to or superior to taxol in the in vitro tublin assembly and B16 Proliferation tests. These tests have been used and relied upon by experimentalists in this field to determine the potential efficacy of a taxol derivative for the treatment of cancer. The data in Table 1 also demonstrates the dramatic difference in activity between structurally similar taxane compounds; see for example, data for compounds 4ab, 3, and 8.

The synthesis, characterization and in vitro test methods for the new taxol derivatives are illustrated by the following examples:

EXAMPLES

Chemistry

All solvents and reagents employed were used as received from the manufacturer except pyridine and acetic anhydride which were distilled prior to use. Reactions were monitored by thin-layer chromatography ("TLC") using 0.20 mm. E. M. Industries silica Gel 60 (aluminum support) silica gel plates. Reactions were also monitored by high pressure liquid chromatography ("HPLC"). Aliqouts of crude reaction mixtures for HPLC analysis were removed from the reaction vessel with a 3 $\mu$l micro-pipette and diluted to 200 $\mu$l in an HPLC sample vial (with insert). The HPLC system consists of a model L-6200 pump, Model AS-4000 or L-3000 UV/VIS/DAD detector (Hitachi Instruments, Inc.). The system was equipped with an NEC 286 computer with 40M hard drive and Lab Manager HPLC software (Hitachi Instruments, Inc.). HPLC columns used included a 4.6 mm.×250 mm. Phenyl column, packed with 5 μm diphenyl material (Supelco, Inc.); a 4.6 mm.×250 mm., 5 μm, 60 angstrom Pentafluorophenyl (PFP) column (ES Industries); and a 4.6 mm.×250 mm. phenyl guard column (Jones Chromatography). The ozone generator used was a Polymetrics Laboratory Ozonator T-816 with an operation at 75 volts, 60 Hertz current, 5.5 psig pressure, and a flow of 2 SLMP delivering a concentration of ozone at 2.2 mg/s. The ozone flow was calibrated using the method described by the manufacturer. Silica gel for flash chromatography (230 to 400 mesh) was supplied by Scientific Products. A Bruker WP-270 and ACE-300, Varian Gemini 400, and a JEOL FX90Q Spectrometer were employed for $^1H$ and $^{13}C$ NMR spectra with chemical shifts reported in ppm. relative to tetramethylsilane using residual non-deuterated NMR solvent for reference. Yields refer to chromatographically pure compounds and are not optimized. Purity of products were judged to be >90% on the basis of spectrophotometric homogeneity unless otherwise stated. Mass spectra were measured at M-Scan Inc. using a VG Analytical 2-SE high field mass spectrometer. Spectroscopic analyses were determined using an Analect Diamond-20 FTIR with an XAD-Plus microscope. The instrument was equipped with an ACR Advanced Logic Research 486 computer with 200M hard drive and an Analect FX80 software package.

EXAMPLE 1

α-Ketoamide 4a

Cephalomannine 3 (178 mg) dissolved in $CHCl_3$ (5 ml) was treated with ozone (2.2 mg/s) for 90 seconds at room temperature followed by evaporation to give a quantitative yield of the isomeric mixture 4ab. Resonances for the major isomer are listed. $^1H$ NMR (90 MHz, $CDCl_3$) 1.11 (s, 3H), 1.21 (s, 3H), 1.29–1.58 (m, 2H), 1.64 (s, 3H), 1.78 (s, 3H), 1.89–2.16 (m, 3H), 2.20 (s, 3H), 2.31 (s, 3H), 2.24 (s, 3H), 2.40–2.72 (m, 1H), 3.75 (d, J=6.8 Hz, 2H), 3.98–4.47 (m, 3H), 4.64 (m, 1H), 4.89 (d, J=8.5 Hz, 1H), 5.13–5.68 (m, 2H), 5.98–6.20 (m, 1H), 6.25 (s, 1H), 7.27–7.73 (m, 8H), 7.85 (d, J=9.4 Hz, 1H), 8.07 (d, J=7.7 Hz, 2H). $^{13}C$ NMR (12 MHz, $CDCl_3$) 9.54, 14.65, 20.76, 21.65, 22.51, 24.37, 26.79, 35.62, 35.62, 43.12, 45.72, 55.00, 58.48, 72.04, 72.04, 73.31, 74.96, 75.58, 76.44, 79.00, 81.16, 84.32, 126.97, 126.97, 128.60, 128.60, 128.60, 128.89, 128.89, 129.16, 130.11, 130.11, 133.24, 133.65, 137.14, 141.68, 159.70, 166.88, 170.30, 171.07, 171.93, 195.94, 203.55. The diagnostic signals in the $^{13}C$-NMR spectrum for the minor isomer in $CDCl_3$ (carbon 6′ of the two diastereomers of 4b) are 102.52 and 105.35 ppm. The diagnostic signals in $CD_3OD$ for 4ab, including solvent addition ($CD_3OD$) to both 4a and 4b are 97.9, 101.9, 104.2, 105.1, and 197.2 ppm for carbon 6′. FTIR (neat, $cm^{-1}$) 981.6 (m), 1025.9 (m), 1070.3 (m), 1108.9 (m), 1178.3 (m), 1241.9 (s), 1373.1 (m), 1724.0 (s), 2900.4 (w), 2940.9 (w), 3064.3 (w), 3413.4 (m), 3490.5 (m). Mass Spectrum (FAB, glycerol/thioglycerol matrix) m/z 821 $(M+1)^+$.

EXAMPLE 2

2′40-Acetyl-α-ketoamide 5 and 2′,7-bis(acetyl)-α-ketoamide 6

Cephalomannine 3 (320 mg) in $CH_2Cl_2$ (4 ml) was treated with ozone (2.2 mg/s) for 205 seconds, purged with nitrogen, and evaporated to dryness. The oxidized cephalomannine in $CH_2Cl_2$ (1.5 ml) was cooled to 0° C. acetic anhydride (0.145 ml) and pyridine (0.156 ml) were added sequentially. The reaction was stirred at 0° C. for 2 hours followed by stirring for an additional 21 hours at room temperature. After diluting with methylene chloride the mixture was washed with 3N HCl (3×), saturated $NaHCO_3$, and brine. The solution was dried over $MgSO_4$, and evaporated. Flash chromatography on silica gel (45/55, 55/45, 75/25 ethyl acetate/hexane) afforded 2 products. The first was 191 mg (58%, white, $R_f$=0.16 50/50 ethyl acetate/hexane) corresponding to 5. $^1H$ NMR (270 MHz, $CDCl_3$) 1.10 (s, 3H), 1.21 (s, 3H), 1.61 (s, 3H), 1.81 (s, 1H), 1.86 (d, J=1.2 Hz, 3H), 2.10 (s, 1H), 2.12 (s, 3H), 2.19 (s, 3H), 2.35 (s, 3H), 2.38 (s, 3H), 1.68–2.58 (m, 4H), 3.76 (d, J=7.0 Hz, 1H), 4.13 (d, J=8.2 Hz, 1H), 4.27 (d, J=8.2 Hz, 1H), 4.35–4.46 (m, 1H), 4.95 (dd, J=1.9, 7.2 Hz, 1H), 5.35 (d, J=4.1 Hz, 1H), 5.57 (dd, J=3.5, 9.7 Hz, 1H), 5.63 (d, J=7.0 Hz, 1H), 6.14 (t, J=9.4 Hz, 1H), 6.24 (s, 1H), 7.25–7.65 (m, 8H), 7.70 (d, J=9.4 Hz, 1H), 8.11 (dd, J=1.8, 7.0 Hz, 2H). $^{13}C$ NMR (68 MHz, $CDCl_3$) 9.78, 14.86, 20.56, 20.99, 22.30, 22.93, 24.60, 26.95, 35.90, 35.90, 43.52, 46.06, 53.39, 58.76, 72.29, 72.49, 74.28, 75.47, 75.90, 76.62, 79.59, 81.31, 84.65, 127.11, 127.11, 129.04, 129.04, 129.22, 129.38, 129.38, 129.70, 130.49, 130.49, 133.19, 134.05, 136.64, 143.04, 159.98, 167.20, 168.21, 170.13, 170.22, 171.62, 196.49, 204.09. FTIR (neat, $cm^{-1}$) 710 (w), 934 (m), 1026 (m), 1070 (s), 1242 (s), 1271 (s), 1373 (s), 1728 (s), 2941 (m), 2960 (m), 3410 (w), 3514 (m). Mass spectra (FAB, m-nitro benzyl alcohol matrix) m/z 863 $(M+1)^+$. The second was 98 mg (28%, white, $R_f$=0.34 50/50 ethyl acetate/hexane) corresponding to 6. $^1H$ NMR (270 MHz, $CDCl_3$) 1.13 (s, 3H), 1.19 (s, 3H), 1.75 (s, 3H), 1.79 (s, 1H), 1.88 (d, J=1.2 Hz, 3H), 1.96 (s, 3H), 2.13 (s, 6H), 1.61–2.34 (m, 3H), 2.37 (s, 3H), 2.38 (s, 3H), 2.47–2.61 (m, 1H), 3.88 (d, J=7.0 Hz, 1H), 4.12 (d, J=8.8 Hz, 1H), 4.29 (d, J=8.2 Hz, 1H), 4.94 (d, J=8.2 Hz, 1H), 5.38 (d, J=3.5 Hz, 1H), 5.46–5.59 (m, 2H), 5.63 (d, J=7.0 Hz, 1H), 6.11 (t, J=9.1 Hz, 1H), 6.18 (s, 1H), 7.28–7.65 (m, 8H), 7.71 (d, J=9.4 Hz, 1H), 8.11 (dd, J=1.8, 7.0 Hz, 2H). $^{13}C$ NMR (68 MHz, $CD_2Cl_2$) 11.05, 14.48, 20.57, 20.86, 21.17, 21.46, 22.88, 24.58, 26.58, 33.58, 35.72, 43.59, 47.44, 53.46, 56.24, 71.77, 72.24, 74.16, 74.91, 75.45, 76.53, 79.17, 81.22, 84.19, 127.13, 127.13, 129.04, 129.04, 129.22, 129.36, 129.36, 129.65, 130.47, 130.47, 133.03, 134.09, 136.69, 141.27, 167.13, 168.32, 168.32, 169.27, 170.06, 170.10, 170.10, 170.46, 202.19. FTIR (neat, $cm^{-1}$) 710 (w), 1049 (m), 1068 (m), 1240 (s), 1269 (s), 1697 (m), 1728 (s), 1751 (s), 2956 (w), 3410 (w), 2523 (bw). Mass spectrum (FAB, m-nitro benzyl alcohol matrix) m/z 905 $(M+1)^+$.

EXAMPLE 3

2′,7-Bis(triethylsilyl)-α-ketoamide 7

To α-ketoamide 4a (75.5 mg) dissolved in pyridine (4.6 ml) was added triethylsilyl chloride (0.31 ml). The reaction mixture was mixed at room temperature for 22 hours followed by $CH_2Cl_2$ dilution. The organic phase was washed sequentially with 3N HCl (2×), saturated $NaHCO_3$, and brine. It was then dried over $MgSO_4$ and evaporated to a solid. Flash chromatography on silica gel (25/75 ethyl acetate/hexane) afforded 39 mg (41%) of a white solid ($R_f$=0.24, 25/75 ethyl acetate/hexane). $^1H$ NMR (300 MHz, $CD_2Cl_2$) 0.35–0.63 (m, 12H), 0.77–0.97 (m, 18H), 1.21 (s, 6H), 1.66 (s, 3H), 1.94 (d, J=1.1 Hz, 3H), 1.81–1.91 (m, 1H), 1.99–2.20 (m, 1H), 2.15 (s, 3H), 2.35 (s, 3H), 2.32–2.42 (m, 1H), 2.50 (s, 3H), 2.51–2.58 (m, 1H), 3.81 (d, J=7.1 Hz, 1H), 4.15 (d, J=8.2 Hz, 1H), 4.29 (d, J=8.4 Hz, 1H), 4.47 (dd, J=6.7, 10.6 Hz, 1H), 4.63 (d, J=2.7 Hz, 1H), 4.95 (m, 1H),5.40 (dd, J=2.7, 9.4 Hz, 1H), 5.67 (d, J=7.2 Hz, 1H), 6.18 (t, J=9.2 Hz, 1H), 6.42 (s, 1H), 7.27–7.44 (m, 5H), 7.49–7.67 (m, 3H), 7.79 (d, J=9.4 Hz, 1H), 8.15 (dd, J=1.5, 7.0 Hz, 2H). $^{13}$C NMR (75 MHz, $CD_2Cl_2$) 4.68, 4.68, 4.68, 5.59, 5.59, 5.59, 6.66, 6.66, 6.66, 6.89, 6.89, 6.89, 10.34, 14.44, 21.01, 21.73, 23.18, 24.58, 26.69, 35.85, 37.57, 43.67, 47.12, 56.01, 58.65, 71.99, 72.67, 75.22, 75.34, 75.43, 76.74, 79.38, 81.36, 84.45, 127.06, 127.06, 128.61, 128.61, 129.04, 129.09, 129.09, 129.09, 129.79, 130.51, 130.51, 134.00, 138.20, 140.53, 160.01, 167.27, 169.44, 170.36, 171.65, 196.76, 201.95. FTIR (neat, $cm^{-1}$) 733 (w), 746 (w), 1003 (m), 1018 (m), 1109 (s), 1138 (m), 1242 (s), 1267 (s), 1369 (m), 1695 (m), 1726 (s), 2877 (m), 2914 (m), 2958 (m), 3028 (w), 3404 (w). Mass Spectrum (FAB, m-nitro benzyl alcohol matrix) m/z 1049 (M+1)+.

EXAMPLE 4

Cephalomannine diol 8

Cephalomannine, 3, was oxidized (stoichiometric reaction) as described by Kingston (Kingston, D. G. I., et al, Modified Taxols, 7. "A Method For The Separation Of Taxol And Cephalomannine", *Journal of Natural Products*, Vol. 55, 259–261, (1992)), incorporated herein by reference. The spectrophotometric analyses correspond to Kingston's reported values.

EXAMPLE 5

α-Ketoamide 4a from diol 8

The diol 8 (79 mg) was dissolved in THF (0.400 ml), and water (0.342 ml) and $NaIO_4$ (59 mg) were added. After stirring for five minutes a white precipitate appeared, and after 20 hours reaction time, analysis by HPLC showed the reaction was complete. It was evaporated on a rotary evaporator, reconstituted with EtOAc/water and separated. The aqueous layer was extracted again with EtOAc and the combined organics were washed with sat. $Na_2SO_3$ and brine. The mixture was dried over $MgSO_4$ and evaporated to yield 62 mg (83%) of a white solid. The data ($^1$H-NMR, $^{13}$C-NMR, IR and FAB-MS) for this sample matched exactly the data for compound 4ab prepared by ozonolysis of cephalomannine (see Example 1).

EXAMPLE 6

α-Ketoamide 4a from cephalomannine 3 via $RuCl_3$/periodate oxidation

Cephalomannine 3 (24.6 mg) was dissolved in carbon tetrachloride (0.06 ml), acetonitrile (0.06 ml), and water (0.092 ml). To this biphasic mixture was added $NaIO_4$ (26.3 mg; 4.1 equivalents) and ruthenium trichloride (0.15 mg, 2.2 mol %) were added. After stirring for five minutes a red/brown precipitate appeared, and after 1 hour the reaction was stopped. It was worked up with methylene chloride, washed with brine, and dried over anhydrous $MgSO_4$. After concentrating to a light yellow solid the sample was analyzed by HPLC. The retention time, peak shape and UV spectrum of the sample was compared with a previously prepared sample of 4ab. The data for this sample matched exactly the data for compound 4ab prepared by ozonolysis of cephalomannine (see Example 1).

EXAMPLE 7

Biological Testing
B16 Melanoma Cell Proliferation

Cells were seeded in 24-well plates at $7.5 \times 10^4$ cells/well and grown in Dulbecco's modified minimal essential medium (MEM) containing 10% bovine calf serum at 37° C. for 24 hours in a 97% humidified atmosphere of 5.5% $CO_2$. The medium was then replaced with fresh medium containing taxol or its derivatives and dissolved in DMSO in concentrations ranging from $7.5 \times 10^{-9}$M to $1 \times 10^{-7}$M for taxol and other derivatives. The final concentration of DMSO in the cell medium was 0.5% or less. This amount of DMSO did not have any effect on cell proliferation as determined from control experiments. After 40 hours, the cells were released by trypsinization and counted in a Coulter counter.

Tubulin Preparation and Assembly

Tubulin free of microtubule-associated proteins was purified from bovine brain as previously described (Algaier, J., Himes, R. H., "The Effect of Dimethyl Sulfoxide on the Kinetics of Tubulin Assembly" *Biochim. Biophys. Acta*, Vol 954, pp 235–243, 1988). The assembly reaction was done at 37° C. in PEM buffer (0.1M Pipes, pH 6.9, 1 mM EGTA, and 1 mM $MgSO_4$) at a protein concentration of 1 mg/ml (10 μM) in the presence of taxol or taxol analogues and 0.5 mM GTP. The reaction was monitored by the increase in the apparent absorbance at 350 nm.

TABLE 1

| Compound[a] | Tubulin Assembly[b] | | B16 Proliferation[c] | |
|---|---|---|---|---|
| | $ED_{50}$[d] | $ED_{50}/ED_{50}$ Taxol | $ED_{50}$[e] | $ED_{50}/ED_{50}$ Taxol |
| 1 | 1.08 | 1.26 | 21.4 | 0.95 |
| 4ab | 1.24 | 1.46[g] | 17.1 | 0.75[g] |
| 3 | 0.70 | 0.82[h] | 33.5 | 1.49[h] |
| 8 | 3.3 | 3.4[i] | >854 | >38[i][j] |
| 5 | >8.54[f] | >10[h] | >854[f] | >38[h] |
| 6 | >8.54[f] | >10[h] | >854[f] | >38[h] |
| 7 | >8.54[f] | >10[h] | >8540[f] | >380[h] |

[a]Methanol (0.5 ml) was added to each vial. Concentrations were determined from the extinction coefficients (absorbance is of a 1% wt./vol. (mg/ml) solution in methanol at 227 nm).

[b]Tubulin at 1 mg/ml was incubated with various concentrations of the compounds at 37° C. for 15 minutes in 0.5 ml of PEM buffer (0.1 M Pipes, 1 mM EGTA, 1 mM $MgSO_4$, pH 6.9). Samples were centrifuged and the protein concentration on the supernatant was determined.

[c]B16 Melanoma cells were incubated with various concentrations of the compounds for about 40h at 37° C.

[d]The concentration in ng/ml which reduces the supernatant protein concentration by 50%.

[e]The concentration in ng/ml which reduces the number of cells by 50% compared to a control.

[f]The highest concentration used without achieving 50% inhibition.

[g]$ED_{50}$ for taxol in the assembly assay was 0.85 μg/ml. In the B16 assay it was 22.7 ng/ml.

[h]$ED_{50}$ for taxol in the assembly assay was 0.854 μg/ml. In the B16 assay it was 22.5 ng/ml.

[i]$ED_{50}$ for taxol in the assembly assay was 0.97 μg/ml. In the B16 assay it was 22.7 ng/ml.

[j]The highest concentration used was 854 ng/ml without achieving 50% inhibition.

What is claimed is:

1. An antineoplastic derivative of taxol having the following formula:

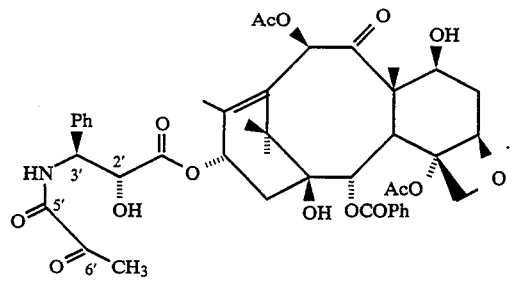

2. A pharmaceutical composition comprising an effective amount of the antineoplastic derivative of claim 1 as an active ingredient, and a pharmaceutically acceptable carrier.

3. A cytotoxic composition comprising an effective amount of:

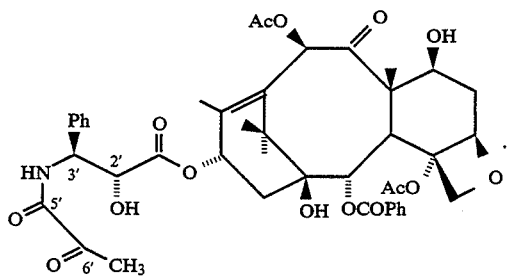

4. A method for inhibiting growth of cancer cells comprising contacting said cells with an effective amount of a composition comprising 5. An antineoplastic derivative of taxol having the following formula:

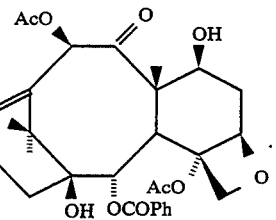

in equilibrium with

* * * * *